(12) United States Patent
Chang et al.

(10) Patent No.: US 10,383,906 B2
(45) Date of Patent: Aug. 20, 2019

(54) METHOD FOR TREATING SKIN DISEASES WITH MANGOSTEEN RIND EXTRACT

(71) Applicant: XANTHO BIOTECHNOLOGY CO., LTD, Taipei (TW)

(72) Inventors: Jia-Ming Chang, New Taipei (TW);
Pei-Yi Tsai, New Taipei (TW);
Ku-Cheng Chen, Taipei (TW)

(73) Assignee: XANTHO BIOTECHNOLOGY CO., LTD., Taipei (TW)

( * ) Notice: Subject to any disclaimer, the term of this patent is extended or adjusted under 35 U.S.C. 154(b) by 0 days.

(21) Appl. No.: 15/743,662

(22) PCT Filed: Jul. 21, 2016

(86) PCT No.: PCT/CN2016/090780
§ 371 (c)(1),
(2) Date: Jan. 10, 2018

(87) PCT Pub. No.: WO2017/016428
PCT Pub. Date: Feb. 2, 2017

(65) Prior Publication Data
US 2018/0200318 A1      Jul. 19, 2018

(30) Foreign Application Priority Data

Jul. 24, 2015   (CN) .......................... 2015 1 0441951

(51) Int. Cl.
*A61K 36/38*   (2006.01)
*A61P 17/00*   (2006.01)

(52) U.S. Cl.
CPC .............. *A61K 36/38* (2013.01); *A61P 17/00* (2018.01)

(58) Field of Classification Search
CPC .......... A61K 36/38; A61Q 19/00; A61P 17/00
See application file for complete search history.

(56) References Cited

U.S. PATENT DOCUMENTS

| 10,251,833 B2 * | 4/2019 | Gan ........................ A61K 8/345 |
| 2006/0105069 A1 * | 5/2006 | Moffett .................... A61K 8/97 424/769 |

OTHER PUBLICATIONS

Man M-Q, et al "Characterization of a Hapten-Induced, Murine Model with Multiple Features of Atopic Dermatitis: Structural, Immunologic, and Biochemical Changes . . . " J. Invest. Dermatol.,2008 (e-pub. Aug. 2, 2007),128(1),pp. 79-86; doi:10.1038/sj.jid.5701011. (Year: 2007).*

Park D, et al "Screening of Anti-Atopic Dermatitis by Using NC/Nga Mouse Whole Blood System" Immune Network, 2008;8(3):98-105 (English Abstract and figures). (Year: 2008).*

* cited by examiner

*Primary Examiner* — Aaron J Kosar
(74) *Attorney, Agent, or Firm* — Hannah Tien

(57) ABSTRACT

A method for treating skin diseases, wherein a composition having an effective amount of mangosteen rind extract is administered.

8 Claims, 6 Drawing Sheets

METHOD FOR TREATING SKIN DISEASES WITH MANGOSTEEN RIND EXTRACT

This application is the 35 USC 371 U.S. National Stage of PCT application PCT/CN2016/090780, which was filed Jul. 21, 2016 and claims priority to China Application No. 201510441951.7 filed on Jul. 24, 2015. The aforementioned applications are incorporated herein by reference in their entirety.

FIELD OF THE INVENTION

The present invention relates to a use of a composition in the preparation of a medicament for treating skin diseases.

BACKGROUND

Skin is the largest organ of the human body. There are many types of skin diseases. Skin diseases may be acute (lasting only a few minutes to several hours) or chronic conditions, which may affect individuals for days, months, years and even the entire life. Skin diseases may be conditions caused by fungal, bacterial, or viral sources, or may be non-infectious, immune responses, such as inflammatory reactions with or without allergens, or idiopathic. Therefore, the symptoms of the skin diseases may vary and range from mild itching, redness and swelling to severe pus and nociceptive pain, for examples damaging ulceration. Skin diseases may impose significant impact on the quality of an individual's life.

Skin diseases may be ulosis, dermatitis, proliferative diseases or conditions, mast cell diseases or conditions, burns, contact with allergens and/or irritants, or inflammatory diseases or conditions, skin diseases including atopic dermatitis, bullous dermatosis, collagenous diseases, psoriasis, psoriatic lesions, contact dermatitis, eczema, urticaria, rosacea, hypertrophic scarring, keloid formation, scleroderma, folliculitis, burns or mucin histiocytosis.

Atopic dermatitis, also known as atopic eczema, is a recurrent allergic skin disease, often associated with genetic disorders, is one of the most common skin diseases in infants and toddlers, accounting for about 3 to 5% of the pediatric population, 60% of these patients develop disease within one year of age, while 30% of patients develop disease between the ages of 1 and 5 years. About half of children suffering from atopic dermatitis also develop allergic rhinitis, asthma, allergic conjunctivitis, etc., also known as allergic children, or known as atopic predisposition.

Psoriasis is a common chronic skin disease, also known as white crust. It is characterized by the appearance of papules, erythema, the surface covered with silver-white scales, clear boundaries, often recurring in scalp, extensor limbs and back.

Folliculitis is suppurative inflammation caused by fungal invasion of follicular parts, which often occurs in heads, necks, buttocks, genitals, perianal areas or other parts of the body, and prone to relapse.

Contact dermatitis is an inflammatory reaction caused by exposure of skin mucosa to external substances, such as chemical fiber clothing, cosmetics, drugs, etc. Its clinical features are sharp-edge-damages to contacted areas, patients with mild conditions suffer from edematous erythema, papules, patients with severe conditions suffer from Molluscum contagiosum (water warts) or even big scars, patients with more serious conditions suffer from epidermolysis, or even necrosis.

The usual ways of treating skin diseases include oral or external formulations. Steroid and antihistamine drugs are now widely used to treat allergic diseases of atopic dermatitis, in severe cases, immunosuppressive agents may be given. However, these methods only show short-term therapeutic effects and are prone to adverse side effects such as skin atrophy, skin depigmentation, acne, osteoporosis, avascular necrosis, arteriosclerosis, glaucoma, enhanced tumor growth, etc. Therefore, there is an urgent need to develop a novel therapeutic agent which may be used for symptom relief and treatment of atopic dermatitis, and provide powerful and long-lasting therapeutic effects with reduced side effects.

Mangosteen has been used in the field of breast cancer prevention and muscle-related diseases, it has also been developed as nutritional supplements and cosmetics in daily lives, as well as uses in the treatment of acute hepatitis, liver fibrosis and cirrhosis prevention (ROC Patent No. 1411432).

Matsumoto et al. have studied α-mangostin, β-mangostin, γ-mangostin, and methyl-β-mangostin purified from mangosteen rinds and investigated the inhibitory effect of this compound at various stages of the cell cycle, showing that this compound has anti-cell proliferative effect and anti-tumor effect (Bioorg. Med. Chem. 2005, 13, 6064-6069).

DETAILED DESCRIPTION OF THE INVENTION

The present invention provides a use of a composition in preparation of a pharmaceutical composition for treating an immune disorder, an allergic disorder or an inflammatory disorder.

Specifically, the present invention provides a use of a composition in preparation of a medicament for treating autoimmune diseases or allergies, wherein the composition comprises an effective amount of extract of mangosteen rind. The drug may also be used for topical treatment use or for precision treatment use.

The present invention further provides a use of a composition in preparation of a medicament for treating autoimmune diseases or allergies, wherein the composition comprises an effective amount of extract of mangosteen rind.

In a preferred embodiment, the mangosteen rind is extracted with a solvent which is selected from the group consisting of methanol, ethanol, n-propanol, 2-propanol, n-butanol, acetone, ethyl acetate and water.

In another preferred embodiment, the extract of mangosteen rind is water extract of mangosteen rind and/or alcohol extract of mangosteen rind.

Mangosteen rind refers to the portion of the mangosteen that is outside the fresh, the rind contains a softer inner rind and a harder outer rind.

In a preferred embodiment, the extract of mangosteen rind is a mangosteen rind water extract; in another preferred embodiment, the extract of mangosteen rind is mangosteen rind alcohol extract.

In a preferred embodiment, the mangosteen rind is the outer rind of the mangosteen rind and/or the inner rind of the mangosteen rind.

In another preferred embodiment, the mangosteen rind is the outer rind of the mangosteen rind.

In a preferred embodiment, the composition further comprises an excipient, wherein the ratio of the excipient is 1% to 10% and the composition still maintains its therapeutic efficacy.

In a preferred embodiment, the water extract of mangosteen rind can stop itching and/or promote cell proliferation; in another preferred embodiment, the mangosteen rind alcohol extract is anti-inflammatory and/or analgesic.

In yet another preferred embodiment, the mangosteen rind extract is capable of inhibiting an increase of the immunomodulatory hormone IL-7, IL-10, but not the pro-inflammatory cytokine IL-1 or TNF-α. The mangosteen outer rind extract mainly inhibits an increase of IL-7 and IL-10, and also inhibits an increase of IL-15 and MCP-1; the mangosteen inner rind extract mainly inhibits an increase of IL-7, IL-10, IL-15, it also inhibits an increase of MCP-1.

In a preferred embodiment, the composition further comprises an oil.

In a preferred embodiment, the compositions of the present invention may be oral or parenteral preparations, the parenteral preparations may be external preparations which may be creams, pastes, ointments, gels, wash lotions or patches.

In a preferred embodiment, the extract of mangosteen rind of the present invention comprises α-mangostin and γ-mangostin, In another preferred embodiment, the water extract of mangosteen rind of the present invention comprises α-mangostin and γ-mangostin.

In yet another preferred embodiment, the alcohol extract of mangosteen rind of the present invention comprises α-mangostin and γ-mangostin.

The composition of the present invention can treat or suppress atopic dermatitis by inhibiting immunomodulatory hormones and not by inhibiting inflammatory cytokines such as IL-1 or TNFα, etc.

Skin diseases include, but are not limited to, atopic dermatitis, bullous dermatosis, collagenous diseases, psoriasis, psoriatic lesions, contact dermatitis, eczema, urticaria, rosacea, hypertrophic scarring, keloid formation, scleroderma, folliculitis, burns or mucin histiocytosis.

As used herein, the term "allergic disorder" refers to a disease, symptom, or condition that is caused by being allergic to non-hazardous substances. Such substances may be present in the environment (e.g., indoor air pollutants and airborne allergens) or not originated from the environment (e.g., those substances that cause skin or food allergies). Allergens can enter the body through many routes, including through breathing, ingestion, skin contact or injection (including insect bites). Many allergic conditions are associated with atopic predisposition to produce IgE antibodies. Because IgE sensitizes mast cells anywhere in the body, individuals with atopic predisposition often manifest the disease in more than one organs. For purposes of the present invention, an allergic disorder includes any allergic reactions that occurs when re-exposed to a sensitizing allergen, which in turn results in the release of inflammation mediators. An allergic disorder includes, but is not limited to, allergic rhinitis (e.g., hay fever), sinusitis, rhinosinusitis, chronic or recurrent otitis media, drug reactions, reactions to insect bites, reactions to latex, conjunctivitis, urticaria, a generalized allergic reaction (anaphylaxis) and an anaphylactoid reaction, atopic dermatitis, asthma and food allergies.

The extract of the present invention can be used in the prevention or treatment of a patient suffering from an inflammatory disorder. As used herein, the term "inflammatory disorder" refers to a disease, a disorder, or a condition characterized by inflammation of the body tissue or having an inflammatory component. It includes a local inflammatory reaction and a systemic inflammation. Examples of such an inflammatory disorder include: transplant rejection, including skin graft rejection; chronic inflammatory disorders of the joints, including arthritis, rheumatoid arthritis, osteoarthritis and skeletal disorders associated with increased bone loss; inflammatory intestinal diseases such as ileitis, ulcerative colitis, Barrett's syndrome and Crohn's disease; inflammatory lung disorders such as asthma, adult respiratory distress syndrome and chronic obstructive pulmonary disease; ocular inflammatory disorders including corneal dystrophy, trachoma, onchocerciasis, uveitis, sympathetic ophthalmitis and endophthalmitis; chronic gingival inflammation disorders including gingivitis and periodontitis; tuberculosis; leprosy; kidney inflammatory diseases, including uremic complications, glomerulonephritis and nephropathy; skin inflammatory disorders, including sclerodermatitis, psoriasis and eczema; central nervous system inflammatory diseases including chronic demyelinating disorders of the nervous system, multiple sclerosis, AIDS-related neurodegeneration and Alzheimer's disease, infectious meningitis, encephalomyelitis, Parkinson's disease, Huntington's chorea, amyotrophic lateral sclerosis, and viral or autoimmune encephalitis; autoimmune disorders, immune complex vasculitis, systemic lupus and erythema; systemic lupus erythematosus (SLE); and cardiac inflammatory diseases such as cardiomyopathy, ischemic heart disease (hypercholesterolemia, atherosclerosis); as well as various other diseases with significant inflammatory components including preeclampsia, chronic liver failure, brain and spinal cord injury, cancer. There may also be generalized inflammation such as Gram-positive or Gram-negative shock, hemorrhagic or anaphylactic shock, or shocks induced by chemotherapy due to reactions to inflammatory cytokines, such as shocks associated with inflammatory cytokines. This shock can be induced, for example, by chemotherapeutic agents used in cancer chemotherapy. As used herein, "treatment of inflammatory disorders" refers to the administration of a compound or composition of the present invention to a subject suffering from, or having symptoms of, or likely to suffer from an inflammatory disorder, in order to treat, alleviate, alter, affect or prevent the inflammatory disorder, symptoms or development thereof.

"Effective amount" is the amount that can achieve effective results when administered to an individual, or that has the desired activity in vivo or in vitro. In the case of inflammatory disorders and autoimmune disorders, as compared to no treatment, effective clinical outcomes include amelioration of the extent or severity of the symptoms associated with the disease or condition, and/or prolonging the life of an individual and/or improvement of the quality of life of the individual. The exact amount of compound administered to an individual will depend on the type and severity of the disease or symptoms and on the individual characteristics such as the general health of the individual, age, sex, weight, and drug tolerance of the individual. It is also dictated by the conditions, severity and types of the inflammatory disorder, the autoimmune disorder and the allergic disorder, or the desired immunosuppressive effect. Those skilled in the art will be able to determine the appropriate dose based on these and other factors. In a preferred embodiment, the effective amount of extract of mangosteen rind is 20 mg/kg to 200 mg/kg.

The present invention relates to an extract or a pharmaceutical composition that are particularly useful in immunosuppression or in the treatment or prevention of inflammation, immune disorders and allergic disorders.

The pharmaceutical composition of the present invention may be formulated into various forms of oral or parenteral preparations. Oral preparations may be formulated as solid preparations such as powders, granules, troches, capsules, etc., or formulated as liquid preparations such as suspensions, emulsions, syrups, etc. Parenteral preparations may be formulated as external preparations such as creams, ointments, gels, wash lotions, patches, etc, or as inhalants, aerosols, suppositories, etc.

The pharmaceutical composition of the present invention may comprise pharmaceutically acceptable excipients, especially may further comprise predetermined solvents or oils, and if desired, may further comprise a dispersant.

Examples of solvents that may be used in the present invention include, but are not limited to, water, ethanol, isopropanol, 1,3-butanediol, propylene glycol, glycerin, etc.

Examples of oils that can be used in the present invention are selected from the group consisting of, but are not limited to, corn oil, sesame oil, flaxseed oil, cottonseed oil, soybean oil, peanut oil, mono-glycerides, di-glycerides, tri-glycerides, mineral oil, squalene, jojoba oil, olive oil, evening primrose oil, borage oil, grape seed oil, coconut oil, sunflower oil, shea butter, and any combinations thereof.

Solvents and oils may be used independently or in any combinations thereof.

Examples of useful dispersants may include, but are not limited to, lecithin, organic monoglycerides, sorbitan fatty acid esters, polyoxyethylene fatty acid esters, sorbitan stearate, etc. These raw materials may also be used independently or in any combinations thereof.

If desired, the composition may further comprise additional materials such as antimicrobials or preservatives.

In the meantime, it is known that an active ingredient may be used simultaneously with the composition as long as it does not have any adverse effects on the pharmaceutical activity of the composition of the present invention. For example, ceramide moisturizers are commonly used as conventional agents for atopic dermatitis, or liquid ingredients such as hydrocortisone steroids, vitamin A derivatives such as vitamin A palmitate and/or tocopherol, etc. may be used with the composition.

When the pharmaceutical composition is used as an external preparation, an appropriate external skin preparation may be used as a base material, and an aqueous solution, a non-aqueous solvent, a suspension, an emulsion or a lyophilized preparation, etc., may be used and sterilized according to known methods.

In practical use of the provided or administered composition of the present invention, the dosage may be determined depending on various factors such as the route of administration, the age, sex, and weight of the patient, the severity of the disease, and the type of medicament as the active ingredient.

In the case where the composition of the present invention may be a food or a cosmetic composition, the composition may be prepared by appropriate addition of at least one food supplement or a cosmetically acceptable carrier.

The food composition can be used in or added to, for example, healthy foods. As used herein, the term "healthy food" refers to a food product containing the composition of the present invention that has an enhanced function as compared to general food products. Healthy foods can be prepared by adding a general food to the composition or by encapsulation, pulverization or suspension liquefaction.

The cosmetic composition may be added independently or in combination with other cosmetic ingredients, or may be appropriately used according to other known methods. Cosmetics include, but are not limited to, aftershaves, lotions, creams, facial masks and color makeups.

Cosmetic compositions can be formulated into various forms of compositions, such as gels, creams, ointments, etc.

The compositions in the form of gels, creams and ointments may be appropriately prepared according to the form of the composition by using known methods, and by addition of known softeners, emulsifiers and thickeners or other materials known in the art.

The gel-form composition can be prepared, for example, by addition of a softener such as trimethylolpropane, polyethylene glycol and glycerol, a solvent such as propylene glycol, ethanol and isocetyl alcohol, and pure water.

The preparation of the compositions in the form of creams can be carried out, for example, by addition of fatty alcohols such as stearyl alcohol, myristyl alcohol, behenyl alcohol, resveratrol, isostearyl alcohol and isocetyl alcohol; emulsifiers such as lipids, such as lecithin, phosphatidylcholine, phosphatidylethanolamine, phosphatidyl serine, phosphoinositide and derivatives thereof, glyceryl stearate, sorbitol palmitate, sorbitol stearate, etc; natural fats and oils such as avocado oil, almond oil, babassu oil, borage oil, *camellia* oil, etc; lipid compositions such as ceramides, cholesterol, fatty acids, phytosphingosine, lecithin, etc; solvents, such as propylene glycol, etc; and pure water.

The preparation of the compositions in the form of ointments can be carried out, for example, by addition of emollients, emulsifiers and waxes, for example microcrystalline wax, paraffin, ceresin, beeswax, spermaceti, petrolatum, etc.

In another aspect, the present invention provides a method for using the composition to prepare a medicament for treating or alleviating atopic dermatitis. As used herein, the term "treating or alleviating" means that when a patient uses a medicament, it stops or delays the course or symptoms of the disease.

EXAMPLES

Example 1: Preparation of Pharmaceutical Compositions

Figure 1:
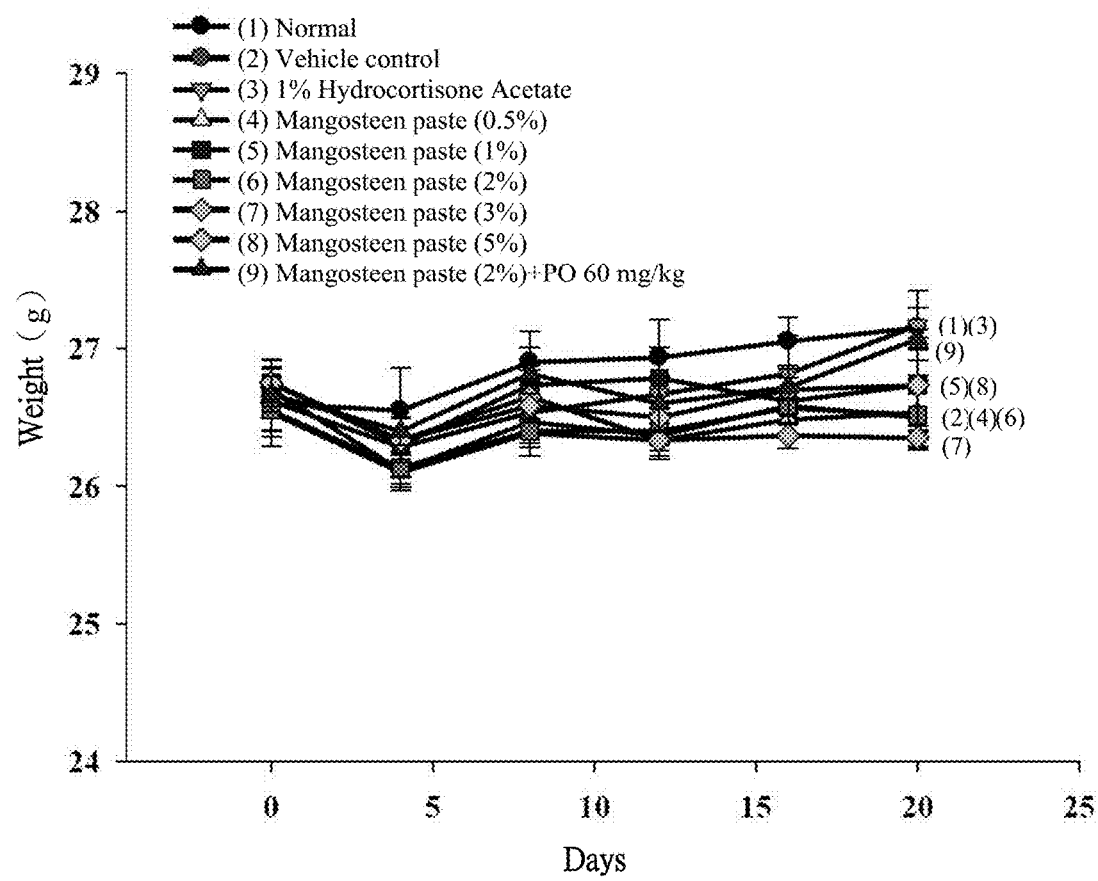
FIG. 1: changes in body weight of the mice in each group.

Mangosteen rind was collected and dried to 50% to 95%, extracted with a solvent (such as water or 10% to 95% alcohol), and concentrated to obtain an extract of mangosteen rind.

The outer rind and inner rind of the mangosteen rind were separated, the outer rind of the mangosteen rind and the inner rind of the mangosteen rind were respectively dried to 50% to 95%, and extracted with a solvent (such as water or 10% to 95% alcohol), then concentrated to obtain an extract of mangosteen outer rind and an extract of mangosteen inner rind.

Different concentrations of pastes or ointments were prepared from the mangosteen rind alcohol and water extract, the mangosteen inner rind, outer rind alcohol and water extract.

Example 2: Animal Experiments

The animals used in the experiments were 8-week-old BALB/c mice (purchased from LESCO Biotech), the body weight were 25 to 28 g and were quarantined by veterinarians for one week before entering the breeding room. The animals were divided into 9 groups, 3 in each group, a total of 27 mices. The temperature of the breeding room was set at 21±2° C., the humidity was set at 30 to 70%, and the environment was set for 12/12 hour light-dark cycle with unlimited supply of food and water.

In the animal experiments, 2-chloro-1,3,5-trinitrobezene (TNCB) was used to induce atopic dermatitis in mice and acetone was used as the solvent to prepare 1% of TNCB which was applied to mice ears (once every 2 days, the volume was 4 ml/kg) one week prior to testings. The test substance (once per day) was started after one week, the given volume was 4 ml/kg, and the mice were continuously induced with TNCB (once every 2 days). In addition, for those groups that were simultaneously provided with test ointments and test oral substances, the oral dose was 60 mg/kg and the volume was 10 ml/kg. When TNCB and the test substance were given on the same day, in order to reduce the effect of interactions between each other, TNCB and test substance were given at least 1 hour apart. The designed experimental groups are shown in the following table. The mangosteen paste of 0.5%, 1%, 2%, 3%, 5% respectively contained 20 mg/kg, 40 mg/kg, 80 mg/kg, 120 mg/kg and 200 mg/kg of extract of mangosteen rind.

TABLE 1

Design of atopic dermatitis animal experiments

| Group | TNCB induction | Test substance given dose/method (daily | Number of animals |
|---|---|---|---|
| Normal | — | solvent//topical smear | 3 |
| Vehicle control | 1% TNCB | solvent/topical smear | 3 |
| 1% hydrocortisone acetate/smear group (Positive control group) | 1% TNCB | 1% hydrocortisone acetate/topical smear group | 3 |
| Mangosteen paste 0.5% | 1% TNCB | Mangosteen paste 0.5%/ topical smear | 3 |
| Mangosteen paste 1% | 1% TNCB | Mangosteen paste 1%/ topical smear | 3 |
| Mangosteen paste 2% | 1% TNCB | Mangosteen paste 2%/ topical smear | 3 |
| Mangosteen paste 3% | 1% TNCB | Mangosteen paste 3%/ topical smear | 3 |
| Mangosteen paste 5% | 1% TNCB | Mangosteen paste 5%/ topical smear | 3 |
| Mangosteen paste 2% + PO 60 mg/kg | 1% TNCB | Mangosteen paste 2%/ topical smear + 60 mg/ kg oral | 3 |

PO: oral administration

Changes in body weight and ear thickness of the mice were monitored twice weekly. Blood of all experimental animals were collected before TNCB induction, after the induction and before the test substance was given and when being sacrificed. After the blood was centrifuged at 3000 rpm for 30 minutes at 4° C., serum samples were obtained and stored.

All animals were sacrificed at the end of the third week after the test substance was given. Mice ears were removed, photographed and stored in 10% of formalin solution for histopathological observation. HE staining was used for the pathological observation (conducted by the National Laboratory Animal Center).

Data are expressed as means±standard deviation (SEM) and Student's t-test was used to compare the differences among treatment groups. Asterisks indicate significant differences, $*p<0.05$; $p<0.01$; $*p<0.001$.

Experimental Results

Body weight: After the formation of atopic dermatitis was induced by TNCB in the mice and one week after the test substance was given to the mice, only slight weight loss as a result of discomfort was observed and there was no statistically significant difference in body weight (FIG. 1).

Figure 2:
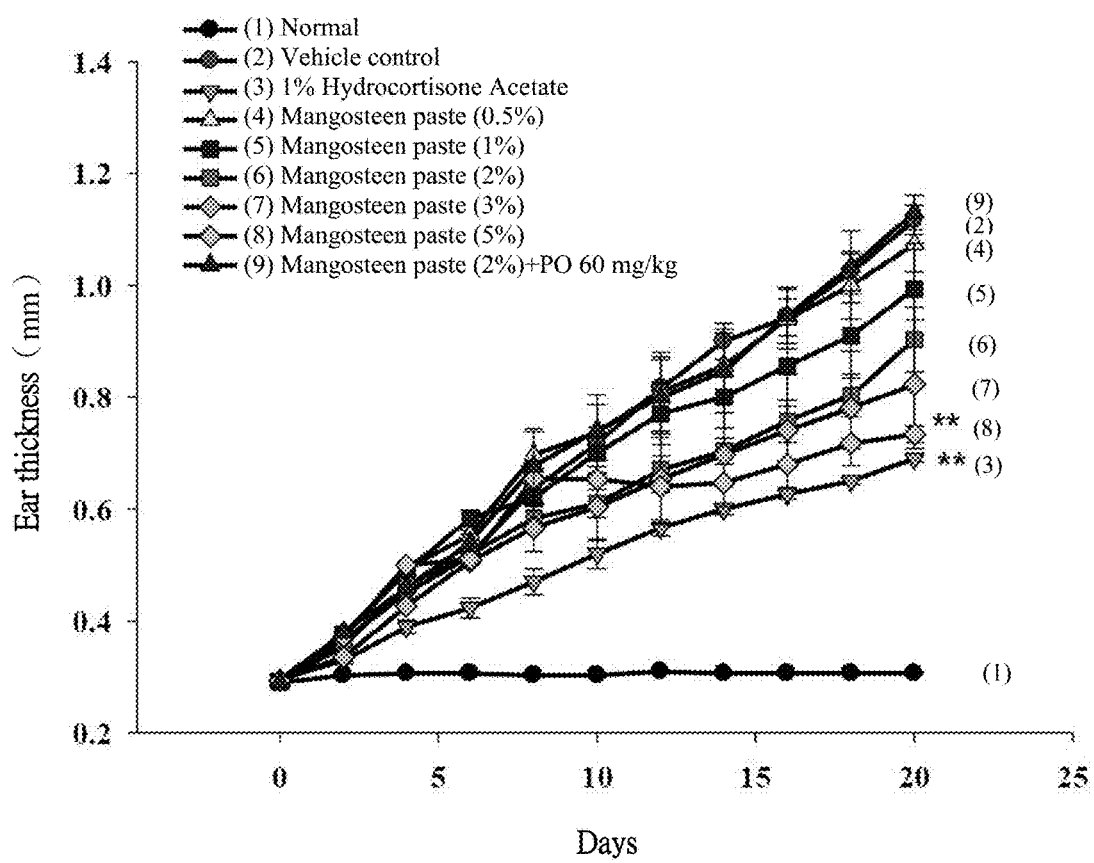
FIG. 2: changes in ear thickness of the mice in each group.

Changes in ear thickness: After atopic dermatitis had been induced, various doses of test ointments were administered to the mice, a decrease in the degree of swelling (thickness) of the mice ears was observed as the dose of the test substance was increased, and when the group receiving a positive control group drug (1% Hydrocortisone acetate) and the group receiving high-dose of test substance (5%) were compared with the model group, 52.7% and 47.3% of inhibition rate (p<0.01) were observed, respectively (Table 2, FIG. 2).

TABLE 2

Inhibition rate (%) of ear thickness and ear weight in experimental groups

| Pathological slice average inflammation degree | Vehicle control group | 1% Hydrocortisone Acetate | Mangosteen paste (0.5%) | Mangosteen paste (1%) | Mangosteen paste (2%) | Mangosteen paste (3%) | Mangosteen paste (5%) | Mangosteen paste (2%) + PO 60 mg/kg |
|---|---|---|---|---|---|---|---|---|
| | 4.67 ± 0.47 | 3 ± 0 | 4.67 ± 0.47 | 5 ± 0 | 4.67 ± 0.47 | 4.33 ± 0.94 | 2.67 ± 0.47 | 5 ± 0 |

Figure 3:
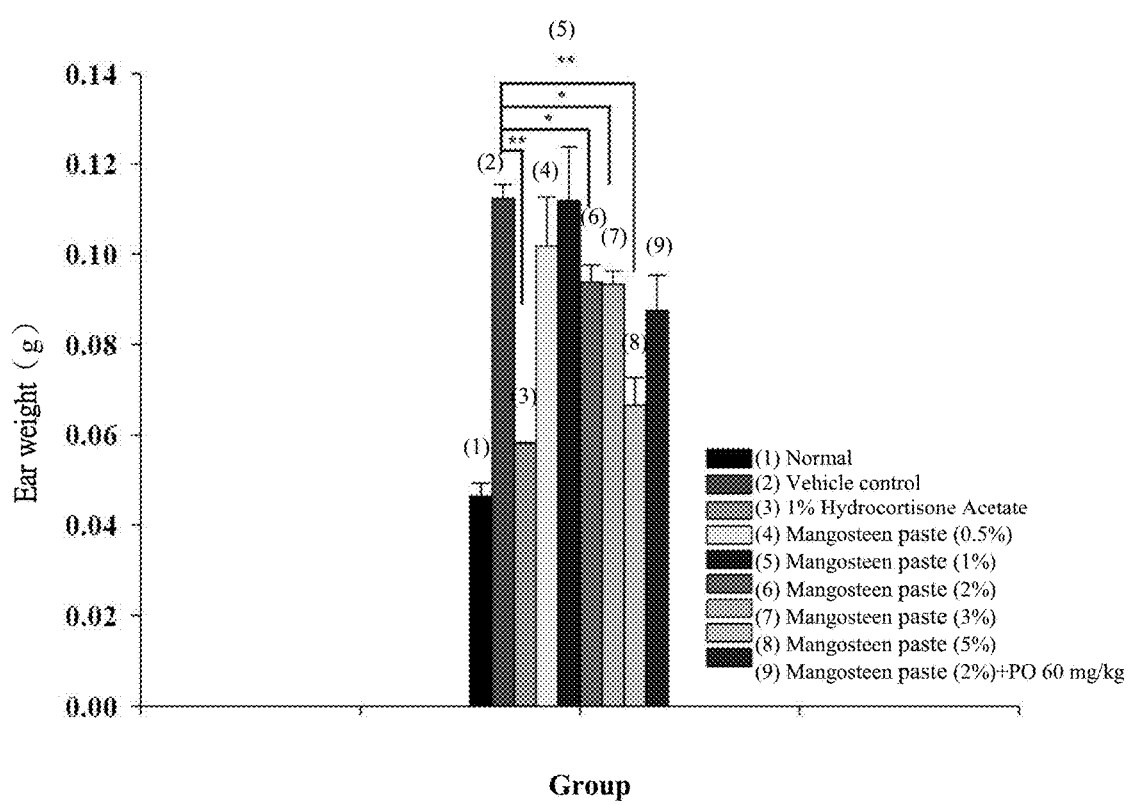
FIG. 3: changes in ear weight of the mice in each group.

Changes in ear weight after sacrifice: Mice ears were removed after the experiment and weighed. It was observed that as the dose of the test substance increased, the weight of the mice ears gradually decreased. The inhibition rate of 82.4% and 69.5% ($p<0.01$) were respectively observed in the groups that received a positive control group drug (1% hydrocortisone acetate) and a high dose of test substance (5%) as compared with the model group. In addition, the inhibition rate of 28.2% and 28.9% were respectively observed in 2% and 3% of the test substances ($p<0.05$) (Table 2, FIG. 3).

Figure 4:
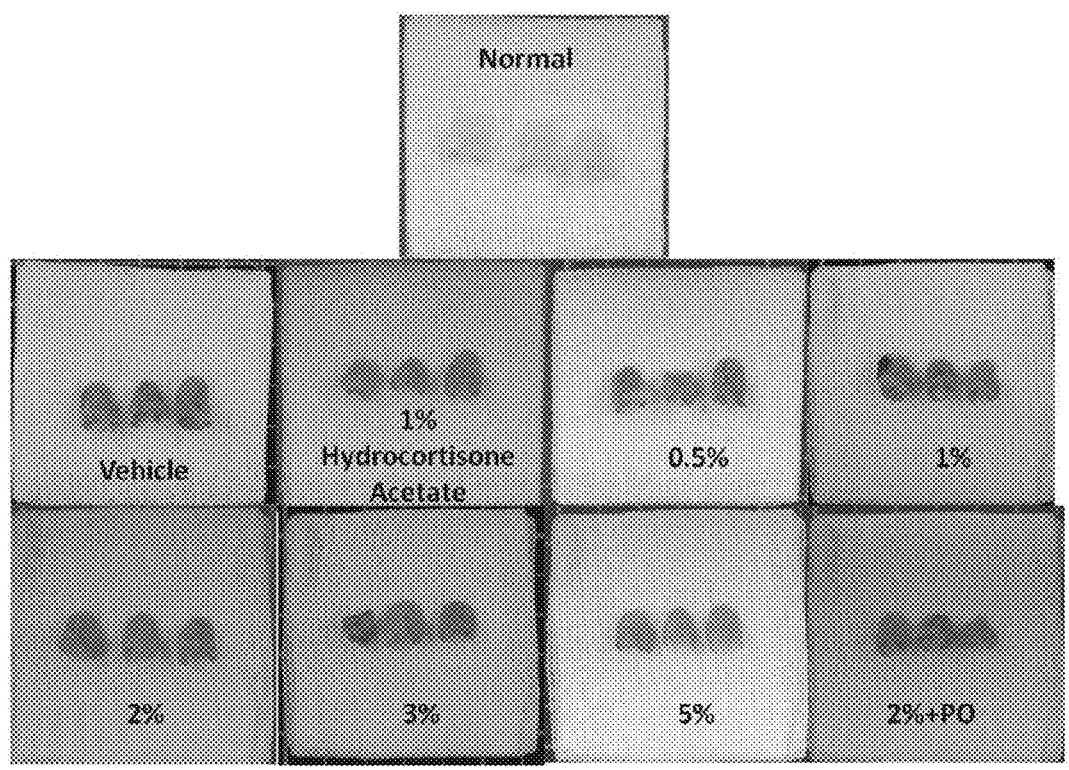
FIG. 4: photos of the mice ears of each group

Ear appearance after being sacrificed: Mice ears were removed for observation of the appearance at the end of 1 experiment, an intact ear contour was found in the group that received a positive control group drug (1% hydrocortisone acetate) and in the group that received a high dose (5%), less surface furfures and roughness were also observed (FIG. 4).

Figure 5:
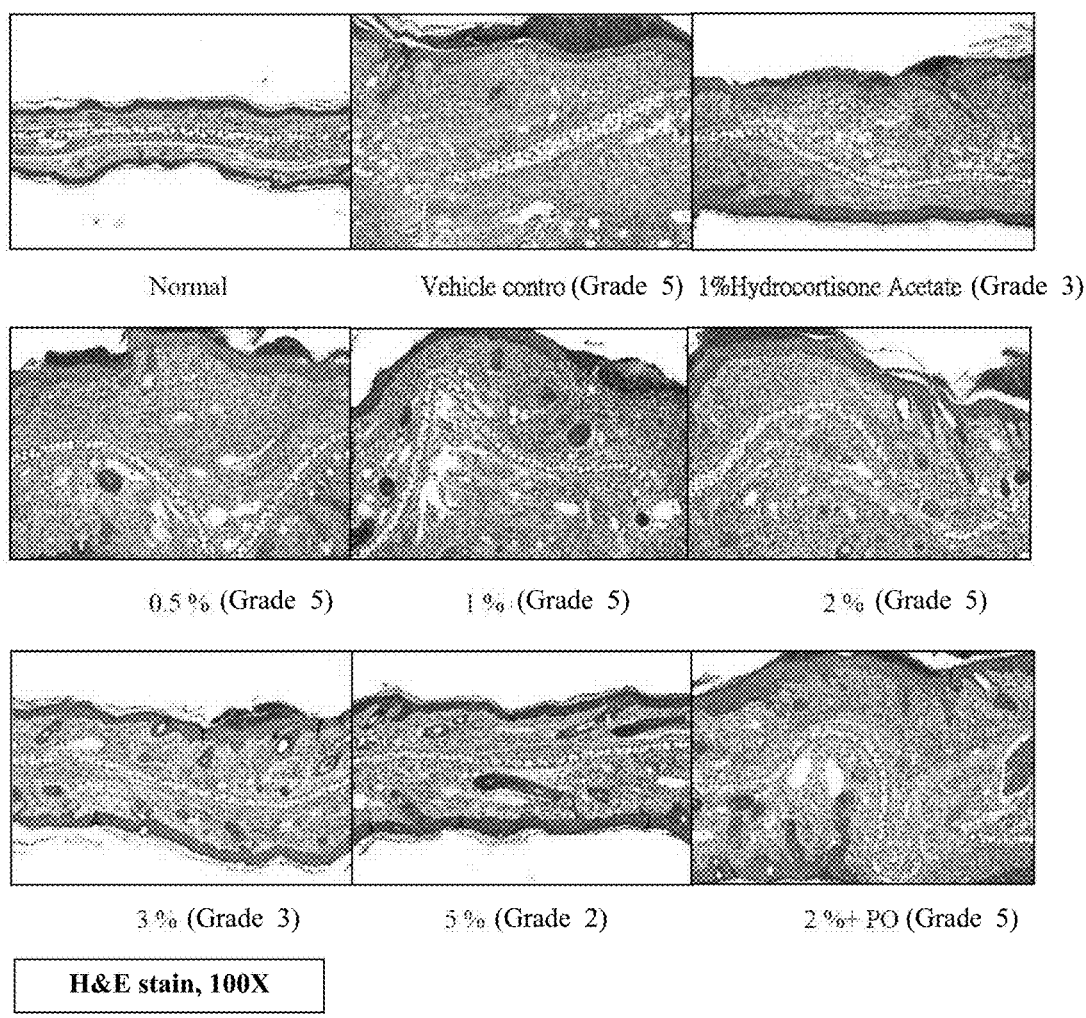
FIG. 5: tissue slices of the mice ears of each group.

Histopathological analysis: The severity of TNCB-induced chronic-active dermatitis was divided into five levels according to the results of the pathological analysis conducted by the National Laboratory Animal Center: minimal (Grade 1), mild (Grade 2), moderate (Grade 3), moderately severe (Grade 4), and extremely severe (Grade 5). The results showed that the average severity of the pathological changes of the vehicle control group, 0.5% group and 2% group was Grade 4.67; the average severity of the pathological changes of the 1% group and 2%+PO 60 mg/kg group was Grade 5; the average severity of the pathological changes of the 3% group was grade 4.33; the average severity of the pathological changes of the positive control drug group (1% hydrocortisone acetate) was Grade 3, and the average severity of the pathological changes of the 5% group was Grade 2.67 (Table 3, FIG. 5).

Example 3: Serum Analysis

Serum was retained when the mice were sacrificed, and biochemical markers (IL-1β, IL-2, IL-4, IL-3, IL-5, IL-7, IL-10, IL-12 (p40), IL-15, IL-17, MCP-1, RANTES, TNF-α) in the serum were analyzed by using the MAGPIX System (Millipore, USA) and the MCYTOMAG Assay Kit (Millipore, USA).

In the atopic dermatitis model, there was a significant increase of IL-7, IL-10, IL-15 and MCP-1, and the mangosteen rind extract was able to inhibit the increase of these markers. The inhibition rates by the mangosteen outer rind extract were 111.7%, 77.1%, 100%, 24%, 16.1%, respectively. The inhibition rates by the mangosteen inner rind extract were 97.0%, 92.8%, 65.6%, 82.7% and 27%, respectively. The results showed that mangosteen rind suppressed atopic dermatitis by inhibition of the immunomodulatory hormones rather than inhibition of pro-inflammatory cytokines IL-1 or TNF-α. Similar to the mode of action of steroid drugs, a part of the immune system could be suppressed, which in turns affected atopic dermatitis. With regard to IL-10, the mangosteen outer rind extract, which completely inhibited IL-10, was significantly superior to the inner rind extract, and IL-10 was an important cytokine formed by the $T_H2$ pathway antibodies. Therefore, mangosteen outer rind extract imposed more significant effects on atopic dermatitis than the mangosteen inner rind extract did. In addition, although the mode of action of mangosteen rind was similar to that of a steroid drug, with regard to IL-15, the steroids were able to inhibit the production of IL-15, but the mangosteen outer rind had more significant effect. The evidence showed that the effect of mangosteen outer rind extract was more specific than that of the steroids and did not act on the entire immune system. Accordingly, the composition and the action mechanism of the mangosteen outer rind extract were not exactly the same as those of the mangosteen inner rind extract.

TABLE 3

Histopathological evaluation of mice ears of experimental groups

| Inhibition rate 1% | 1% Hydro-cortisone Acetate | Mangosteen paste (0.5%) | Mangosteen paste (1%) | Mangosteen paste (2%) | Mangosteen paste (3%) | Mangosteen paste (5%) | Mangosteen paste (2%) + PO 60 mg/kg |
|---|---|---|---|---|---|---|---|
| Ear weight | 82.4 | 16.1 | 0.8 | 28.2 | 28.9 | 69.5 | 37.8 |
| Ear thickness | 52.7 | 5.3 | 15.2 | 26.3 | 36.2 | 47.3 | −1.6 |

Mangosteen inner rind and outer ring extract analysis: According to the results of pathological slices conducted by the National Laboratory Animal Center, the severity of TNCB-induced chronic-active dermatitis was divided into five levels: minimal (Grade 1), mild (Grade 2), moderate (Grade 3), moderately Severe (Grade 4), and extremely severe (Grade 5). The results showed that the outer rind had an effect better than the inner rind (Table 4).

TABLE 4

Ear thickness and ear weight inhibition rate (%) of experimental groups

| Inhibition rate (%) | 1% Hydrocortisone Acetate | Mangosteen outer rind (4%) | Mangosteen inner rind (4%) |
|---|---|---|---|
| Ear weight | 68.91 | 54.62 | 36.047 |
| Ear thickness | 50.75 | 40.04 | 24.84 |

TABLE 5

Inhibition rate of various markers in serum

| | IL-7 | IL-10 | IL-15 | MCP-1 |
|---|---|---|---|---|
| extract of mangosteen outer rind | 77.1% | 100% | 24% | 16.1% |
| extract of mangosteen inner rind | 92.8% | 65.6% | 82.7% | 27% |
| Steroid | 62.7% | 88% | 125.1% | 32.1% |

The results of above examples showed that the composition of the present invention had a significant effect on atopic dermatitis.

Example 4: High Performance Liquid Chromatography Analysis of Alcohol Extract of Mangosteen Rind The chemical fingerprints spectrum of the alcohol extract of mangosteen rind was analyzed by using a high performance liquid chromatography (HPLC). 300 mg±1 mg of alcohol extract of mangosteen rind was weighed and placed in a 100 mL volumetric flask and diluted to 100 mL with a diluent, which was shaked by ultrasonic waves for at least 60 min until completely dissolved, allowed to stand at room temperature. After the temperature was raised and the oil-like material at the bottom was shaken and homogenized, 2 mL of solution was removed from the 100 mL flask and transferred to a 20 mL volumetric flask, after the volume was fixed with a diluent to 20 mL, a 0.45 μm of PVDF membrane was used for filtration.

Figure 6:
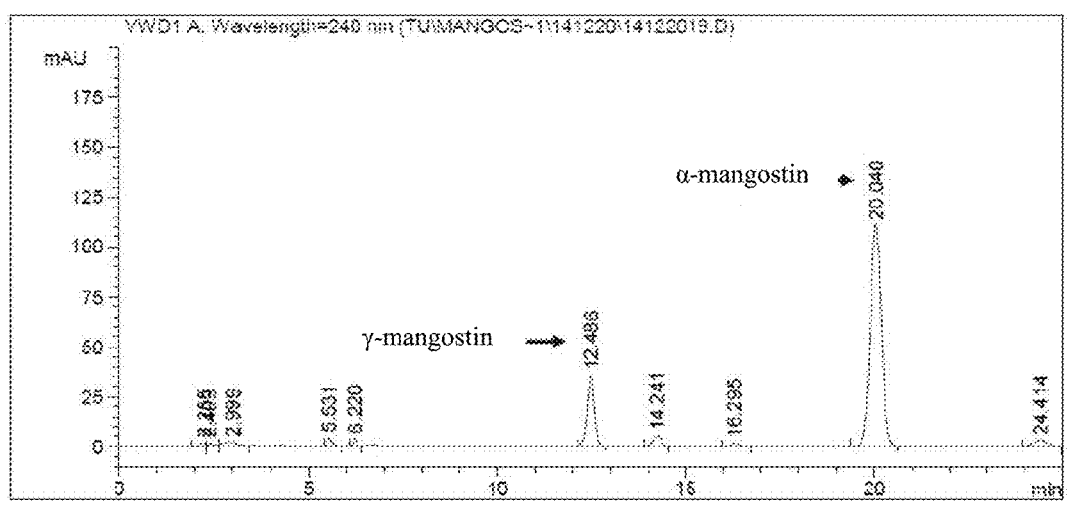
FIG. 6: HPLC spectrum of the alcohol extract of mangosteen rind.

An AGILENT/1100 series high performance liquid chromatography (HPLC) system equipped with a PDA detector and an autosampler was used to perform high performance liquid chromatographical analysis. The temperature of the column (COSMOSIL MS-II, 5 um, 4.6×250 mm, Waters) was maintained at 30° C. during the analysis. A 10 L sample was introduced into the HPLC system. An acetonitrile-water −0.2% phosphoric acid eluent system (ACN/$H_2O$=72/28 (v/v), w/0.2% $H_3PO_4$) was used to perform the chemical fingerprint analysis at a flow rate of 1.0 ml/min and the peak detection was performed at a detecting wavelength of UV 240 nm. FIG. 6 shows the HPLC chemical fingerprint spectrum analysis of the alcohol extract of mangosteen rind. The results showed that the alcohol extract of mangosteen rind had HPLC peaks with the following retention times (Table 6).

TABLE 6

HPLC spectrum wave peaks of alcohol extract of mangosteen rind

| Number of wave peaks | Retention time (minute) |
| --- | --- |
| 1 | 5.53 |
| 2 | 6.22 |
| 3 | 12.48 |
| 4 | 14.24 |
| 5 | 16.29 |
| 6 | 20.04 |
| 7 | 24.41 |

What is claimed is:

1. A method for treating atopic dermatitis induced by overexpression of Th2, comprising administering a composition of an effective amount of extract of mangosteen rind to a subject suffering from atopic dermatitis induced by overexpression of Th2, wherein the administration of the effective amount of extract of mangosteen rind is parenteral injection.

2. The method of claim 1, wherein the extract of mangosteen rind is water extract of mangosteen rind and/or alcohol extract of mangosteen rind.

3. The method of claim 1, wherein the mangosteen rind is outer rind of the mangosteen rind and/or inner rind of the mangosteen rind.

4. The method of claim 1, wherein the mangosteen rind is outer rind of the mangosteen rind.

5. The method of claim 1, wherein the extract of mangosteen rind comprises α-mangostin and γ-mangostin.

6. The method of claim 1, wherein the composition further comprises an excipient, and ratio of the excipient is 1% to 10%.

7. The method of claim 1, wherein the composition is capable of inhibiting an increase of IL-7, IL-10, IL-15 or MCP-1.

8. The method of claim 1, wherein the composition is an external preparation.

* * * * *